US012753156B2

(12) United States Patent
Barreca et al.

(10) Patent No.: US 12,753,156 B2
(45) Date of Patent: Oct. 6, 2026

(54) SOLID STATE FORM OF TAFAMIDIS AND A PROCESS FOR ITS PREPARATION

(71) Applicant: Quimica Sintetica, S.A., Alcalá de Henares (ES)

(72) Inventors: Giuseppe Barreca, Sirtori (IT); Luca Carcone, Milan (IT); Piero Paravidino, Sedriano (IT); Daniele Pengo, Senago (IT); Massimo Zampieri, Casano Maderno (IT); Liming Huang, Hangzhou City (CN)

( * ) Notice: Subject to any disclaimer, the term of this patent is extended or adjusted under 35 U.S.C. 154(b) by 382 days.

(21) Appl. No.: 18/288,195

(22) PCT Filed: Apr. 22, 2022

(86) PCT No.: PCT/EP2022/060716
§ 371 (c)(1),
(2) Date: Oct. 25, 2023

(87) PCT Pub. No.: WO2022/229026
PCT Pub. Date: Nov. 3, 2022

(65) Prior Publication Data

US 2024/0208915 A1 Jun. 27, 2024

(30) Foreign Application Priority Data

Apr. 26, 2021 (EP) .................................... 21382362

(51) Int. Cl.
*C07D 263/57* (2006.01)

(52) U.S. Cl.
CPC ................................ *C07D 263/57* (2013.01)

(58) Field of Classification Search
CPC ................................................... C07D 263/57
See application file for complete search history.

(56) References Cited

FOREIGN PATENT DOCUMENTS

| | | | | | |
|---|---|---|---|---|---|
| WO | 2013038351 | A1 | 3/2013 | | |
| WO | 2016038500 | A1 | 3/2016 | | |
| WO | WO 2016/038500 | * | 3/2016 | .......... | C07D 263/57 |
| WO | 2019175263 | A1 | 9/2019 | | |
| WO | 2020232325 | A1 | 11/2020 | | |
| WO | WO 2020/232325 | * | 11/2020 | .......... | C07D 263/57 |
| WO | 2021001858 | A1 | 1/2021 | | |
| WO | 2021152623 | A1 | 8/2021 | | |
| WO | 2022084790 | A1 | 4/2022 | | |

OTHER PUBLICATIONS

Mino R. Caira, Crystalline Polymorphism of Organic Compounds, Topics in Current Chemistry, vol. 198, pp. 163-208, XP008166276, ISSN: 0340-1022 (1998). (Year: 1998).*
Bulawa et al. "Tafamidis, a potent and selective transthyretin kinetic stabilizer that inhibits the amyloid cascade", Proc. Natl. Acad. Sci USA, Jun. 2012, 109(24), pp. 9629-9634.
Mino R. Caira "Crystalline Polymorphism of Organic Compounds", Topics in Current Chemistry, vol. 198, Jan. 1, 1998, pp. 163-208.
Razavi et al. "Benzoxazoles as Transthyretin Amyloid Fibril Inhibitors: Synthesis, Evaluation, and Mechanism of Action", Angewandte Chemie Int. Ed. 2003, 42, 2758-2761.

* cited by examiner

*Primary Examiner* — Erich A Leeser

(57) ABSTRACT

A crystalline form of 2-(3,5-dichlorophenyl)-1,3-benzoxazole-6-carboxylic acid and a method for its preparation are described. The crystalline form is further suitable as intermediate compound to prepare Form 1, Form 4 and Form M with improved stability and purity.

14 Claims, 12 Drawing Sheets

SOLID STATE FORM OF TAFAMIDIS AND A PROCESS FOR ITS PREPARATION

FIELD OF THE INVENTION

The present invention relates to a crystalline form of tafamidis and to a method for its preparation.

BACKGROUND ART 2-(3,5-dichlorophenyl)-1,3-benzoxazole-6-carboxylic acid (tafamidis) is a drug used to delay loss of peripheral nerve function in adults with familial amyloid polyneuropathy, a fatal, although relatively rare disease linked to a hereditary mutation of the transtyhetin (TTR) gene, and for the treatment of heart disease (cardiomyopathy) caused by transthyretin mediated amyloidosis (ATTR-CM).

In May 2019, the FDA approved two separate preparations for oral administration, one containing Tafamidis (Vyndamax®) and one containing Tafamidis Meglumine (Vyndaqel®), for the treatment of the cardiomyopathy of wild-type or hereditary transthyretin-mediated amyloidosis (ATTR-CM) in adults to reduce cardiovascular mortality and cardiovascular-related hospitalization.

As generally known, an active principle may exist under amorphous or different crystalline forms (polymorphs), either as pure compound or in forms in which molecules of water (hydrates) or of another solvent (solvates) are present in the structure of the crystal. In case of hydrates and solvates, the ratio between the number of molecules of active principle and molecules of water or solvent may vary, giving rise to different solid forms of the compound.

In particular, amorphous solids consist of disordered arrangement of molecules and do not possess a distinguishable crystal lattice.

A specific solid form of a compound may possess physical properties that differ from, and are advantageous over, those of other crystalline modifications. These include, but are not limited to, packing properties such as molar volume and density, thermodynamic properties such as melting point and glass transition temperature and solubility, kinetic properties such as dissolution rate, surface properties such as wettability interfacial tension, handling and filtration properties. Variations in any of these properties may affect the chemical and pharmaceutical processing of a compound and may often render a specific solid form more suitable than others for pharmaceutical and medical use or for preparing other polymorphic forms in a high yield and with good degree of purity.

2-(3,5-dichlorophenyl)-1,3-benzoxazole-6-carboxylic acid was first described in WO 2004/056315 (filed on 19 Dec. 2003), wherein tafamidis is disclosed as compound (19) and obtained as a white solid, by final isolation of the acid via preparative TLC.

WO 2016/38500 discloses various crystalline forms of tafamidis (6-carboxy-2-(3,5-dichlorophenyl)-benzoxazole, namely form 1, form 2 (THF solvate), form 4, form 6 and an amorphous form.

As used herein, "tafamidis form 4" refers to the form described in WO 2016/38500 and characterized by a powder X-ray diffraction pattern comprising peaks at diffraction angles (2-theta) of 15.9, 16.9 and, optionally, also 18.0, 24.1 and 27.3 (all±0.2).

As used herein, "tafamidis form 1" refers to the form described in WO 2016/38500 and characterized by a powder X-ray diffraction pattern comprising a peak at diffraction angle (2-theta) of 28.6 and further comprising other peaks at 15.4, 16.5, 20.2, 23.5, 26.7, 29.0 (all±0.2).

WO 2013/038351 describes the N-methyl-D-glucamine (meglumine) salt of tafamidis, specifically the anhydrous form I, also referred to as form M, having a powder X-ray diffraction pattern comprising peaks at diffraction angles (2-theta) of 10.7, 11.8 and 13.3 (all±0.2, using Cu $K\alpha_1$ radiation), that is the solid API form present in the medicinal product Vyndaqel according to the EPAR—public assessment report issued by the European Medicine Agency (EMA) in date 22 Sep. 2011.

The article published on *Angewandte Chemie Int. Ed.* 2003, 42, 2758-2761 describes a method for obtaining tafamidis by concentration in vacuo of flash column chromatography fractions (4.9:95:0.1 MeOH:$CH_2Cl_2$:AcOH). According to the information provided during the examination of EP 3191461, the thus-obtained solid is amorphous and, upon storage for 1 week at 70° C. and 75% relative humidity, it converts into crystalline form 4.

Various solid forms of tafamidis, including adducts with formic acid, trifluoroacetic acid and acetic acid, have been described in WO 2019/175263.

WO 2020/232325 is related to tafamidis and describes an amorphous form, form I (hydrate form, obtained by exposure of the amorphous form to water vapours for 30-33 days or from THF/water), form II (from 2-methylTHF, obtained by crash cooling or by slow evaporation of solvent over 7 days), forms III and IV (solvate with acetic acid) and form V (anhydrous or solvated with methanol). Forms I, II, III and IV convert into form 4 when dried in vacuum dryer at 100-160° C. as disclosed in examples from 16 to 20 of WO 2020/232325.

Form 1 is the thermodynamically stable form at room temperature, as reported in the prosecution history of European counterpart of WO 2016/38500, while form 4 is more stable, as reported above, at high temperature. It is clear that the methods for the preparation of forms 1 and 4 of tafamidis and of form M of tafamidis meglumine described in the documents cited above are related to laboratory scale trials (10 mg to 1-1.5 grams) and have not been demonstrated to be suitable for the production on large scale. There is a need for an alternative robust and easily industrializable process for the preparation of tafamidis polymorphic forms, especially crystalline form 1 and crystalline form 4, and also tafamidis meglumine salt in its polymorphic form M, the form of tafamidis present in the medicament Vyndaqel®. An object of this invention is to provide new crystalline form of tafamidis which is suitable to be produced on large scale and to be converted into other crystalline forms and other salts of tafamidis or, if required, directly incorporated as such in a pharmaceutical dosage form.

SUMMARY OF THE INVENTION

These objectives described above are achieved with the present invention that, in one aspect thereof, relates to a new crystalline form of 2-(3,5-dichlorophenyl)-1,3-benzoxazole-6-carboxylic acid (tafamidis), hereafter also referred to as form alpha, said substantially pure and stable crystalline form being characterized by an XRPD profile comprising at least one of the peaks at 9.6, 13.5, 16.3, 18.2, 20.4 and 27.5 degrees 2θ, when collected with the Kα radiation of copper (λ=1.5418 Å).

In another aspect, the present invention relates to a process for the preparation of the crystalline form alpha of 2-(3,5-dichlorophenyl)-1,3-benzoxazole-6-carboxylic acid.

In further aspect, the invention relates to the use of form alpha of 2-(3,5-dichlorophenyl)-1,3-benzoxazole-6-carboxylic acid for the preparation of a solid forms of 2-(3,5-dichlorophenyl)-1,3-benzoxazole-6-carboxylic acid other than form alpha and a salt or adduct thereof.

In another aspect, the present invention is related to a pharmaceutical formulation comprising form alpha of 2-(3,5-dichlorophenyl)-1,3-benzoxazole-6-carboxylic acid as described above.

DETAILED DESCRIPTION OF THE INVENTION

Figure 1:
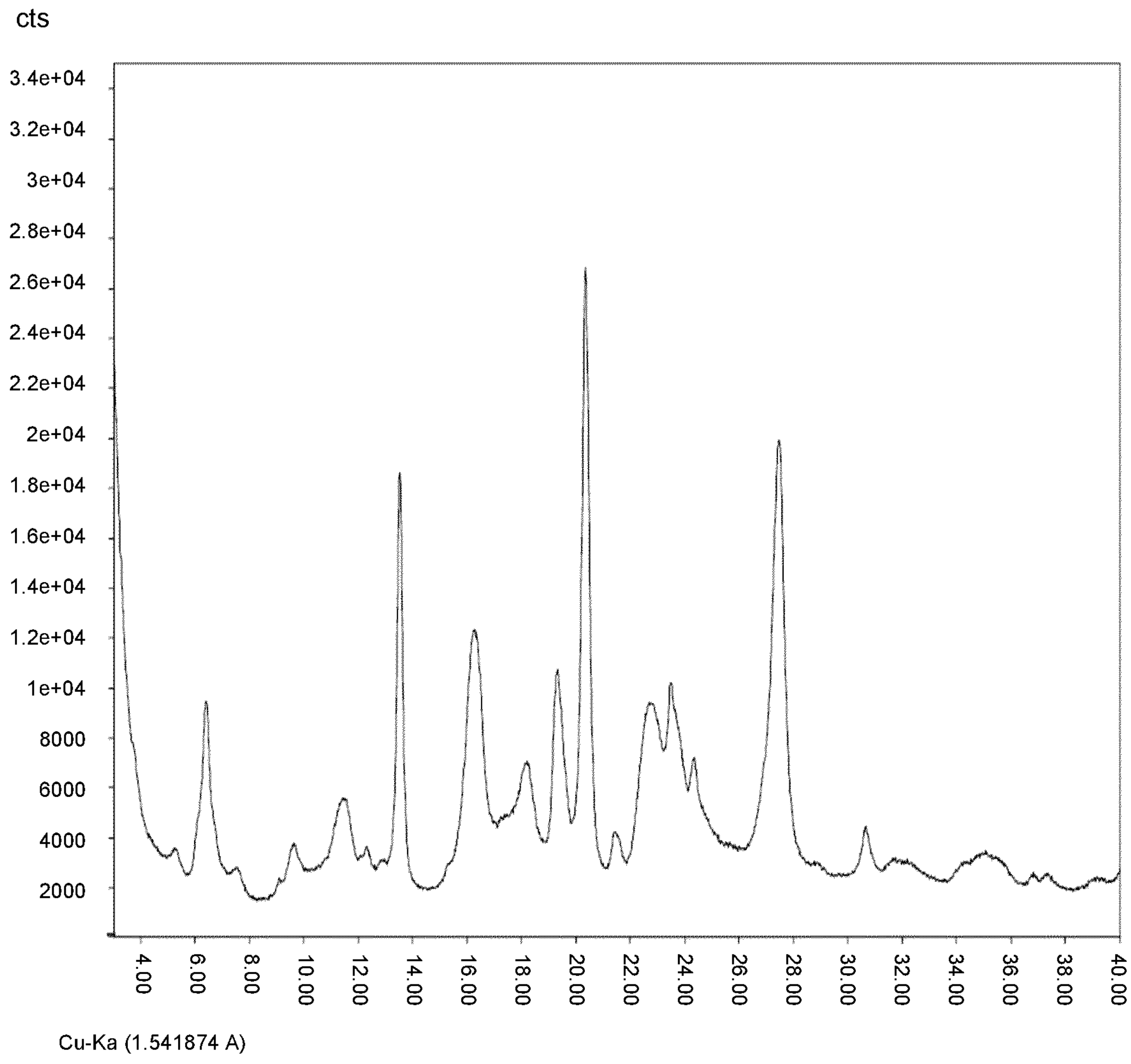
FIG. 1 depicts an exemplary X-ray powder diffractogram (XRPD) of the solid form alpha of 2-(3,5-dichlorophenyl)-1,3-benzoxazole-6-carboxylic acid.
Figure 2:
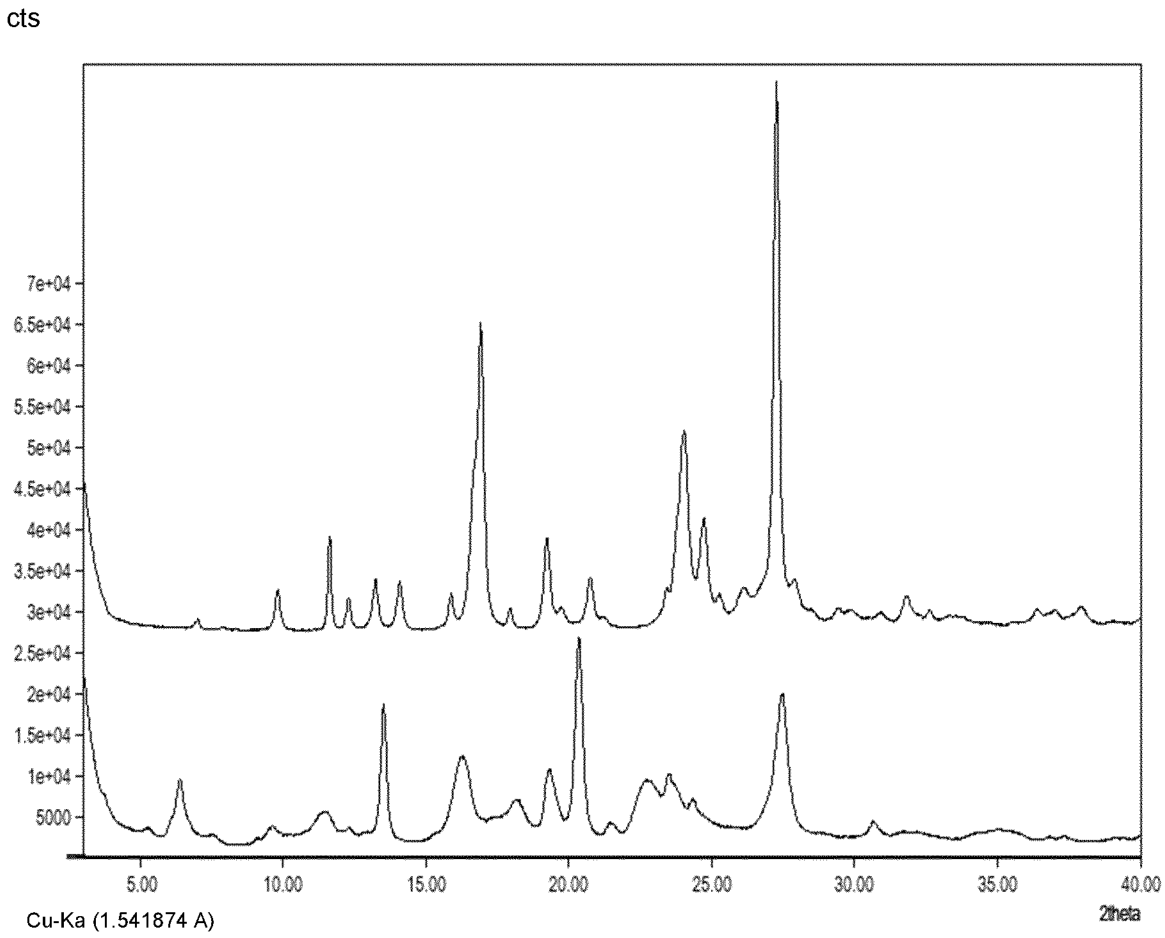
FIG. 2 shows a comparison of the XRPD patterns of form alpha (lower curve) and of form 4 (upper curve) of 2-(3,5-dichlorophenyl)-1,3-benzoxazole-6-carboxylic acid.

All terms used in this application, unless otherwise specified, are to be understood in their ordinary meaning as known in the technical field.

The term "about" includes the range of experimental errors, which can normally occur performing a measurement, e.g. +5% or +2% or +1%.

The term "mass" defines the combination of substrates, reagents, solvents, and products on which a physical or chemical transformation is carried out.

The term "excipient" means any substance contained in the final pharmaceutical form other than the active ingredient and which generally may not be therapeutically effective by itself. Excipients are essential for the administration of the active substance, as they allow to deliver the drug to the target site. Excipients are commonly referred to as raw materials entering into the composition of a pharmaceutical preparation with the aim of giving a shape, to facilitate administration and preserve the active ingredient. Furthermore, they contribute to characterize the pharmaceutical preparation from the point of view of appearance, stability, biopharmaceutical profile and acceptability by the patient.

Unless otherwise indicated, in the context of the present invention the percentage and amount of a certain component in a composition are to be referred to the weight of said component with respect to the total weight of the composition.

Unless otherwise indicated, in the context of the present invention the indication that a composition "comprises" other one or more components/elements means that the indicated components/elements must be present and also other components may be present, but are not necessarily present, in the composition, in addition to the ones specifically recited. In other words, the indication that a composition "comprises" one or more components does not exclude that the composition consists of, or consists essentially of, the recited component(s).

As used herein, the term "substantially pure" with reference to a particular crystalline form means that the crystalline form includes less than 10%, preferably less than 5%, more preferably less than 3%, even more preferably less than 1% by weight of any other physical forms of the compound.

As used herein, the indication that a compound or composition A is "pure" or "entirely free" of other substances (or "consists of") means that, within the detection range of the instrument or method being used, no substances other than those specifically indicated can be detected in A.

As used herein, the term "a compound or composition A is essentially free of other substance(s)", or "consists essentially of A", means that only trace amount of substance(s) other than A, if any, can be detected using the analytical methods and techniques known to the person skilled in the art.

Unless otherwise indicated, in the context of the present invention a range of values indicated for a certain parameter, for example the weight of a component in a mixture, includes the upper and the lower limits of the range, e.g. if the content in weight, or in volume, of a component A in a mixture is indicated as "X to Y", the content of A can be X, Y or any of the intermediate values.

By "polymorphically stable" it is meant that the crystalline form of the present invention, when stored (I) at 70° C. under reduced pressure for at least 1 hour (preferably for 5 hours, more preferably for 10 hours, even more preferably for 12 hours), (II) at 60° C. for at least 1 day (preferably for 5 days, more preferably for 10 days, even more preferably for 15 days), (III) at 40° C. and 75% relative humidity (RH) for at least 1 day (preferably for 8 days, more preferably for 15 days, even more preferably for 1 month, advantageously for 6 months), and/or at room temperature and relative humidity (RH) not more than 80% for at least 5 days (preferably for 1 month, more preferably for 8 months, even more preferably for 10 months), shows no signs of transformation into a different crystalline form as evaluated by the absence of peaks in an X-ray powder diffractogram (XRPD).

By "chemically stable" it is meant that the solid form of the present invention shows no degradation upon storage under stressed conditions, e.g. when stored (I) at least 70° C. under reduced pressure for at least 1 hour (preferably for 5 hours, more preferably for 10 hours, even more preferably for 12 hours), (II) at 60° C. for at least 1 day (preferably for 5 days, more preferably for 10 days, even more preferably for 15 days), (III) at 40° C. and 75% relative humidity (RH) for at least 1 day (preferably for 8 days, more preferably for 15 days, even more preferably for 1 month, advantageously for 6 months), and/or at room temperature and at relative humidity (RH) not more than 80% for at least 5 days (preferably for 1 month, more preferably for 8 months, even more preferably for 10 months).

"No degradation" means that a HPLC analysis of the sample shows no significant worsening of the purity, in terms of formation of new impurities and increase of the content of those already present profile with respect to the initial profile (for example, less than 0.1% area increase).

"Storage condition" referred to 2-(3,5-dichlorophenyl)-1,3-benzoxazole-6-carboxylic acid and its salt means that all the forms are stored in a close vessel at room temperature, ambient pressure and at relative humidity (RH) degree not more than 80%.

"Type A" container, used in stability studies, is referred to a zip closure transparent double polyethylene bags collected in a plastic (HPDE) drum.

"Type B" is referred to an additional stability container consisting of zip closure transparent double polyethylene bags inserted into quadruple laminated Aluminium bag heat sealed.

Room temperature is referred to a range of temperature between 15-25° C., as reported in the European Pharmacopoeia.

Unless otherwise indicated, the data related to the peaks in the XRPD pattern are meant within the common uncertainty due to the instrument measurement, typically ±0.2 degrees 2θ, when collected with the Kα radiation of copper (λ=1.5418 Å).

The present invention provides, in one embodiment, a crystalline form of 2-(3,5-dichlorophenyl)-1,3-benzoxazole-6-carboxylic acid designated as form alpha, characterized by an XRPD profile comprising at least one of the peaks at 9.6, 13.5, 16.3, 18.2, 20.4 and 27.5 degrees 2θ (±0.2), when collected with the Kα radiation of copper (λ=1.5418 Å).

Preferably, said crystalline form of 2-(3,5-dichlorophenyl)-1,3-benzoxazole-6-carboxylic acid is further characterized by an XRPD profile additionally comprising at least one of the peaks at 5.3, 6.4, 12.3, 19.3, 22.8 and 23.5 degrees 2θ (±0.2).

As a non-limiting example, a full peak list of a representative form alpha XRPD pattern is provided hereunder (I/I0=relative intensity):

| No. | 2theta [°] | d [Å] | I/I0 |
|---|---|---|---|
| 1 | 3.81 | 23.1984 | 10.16 |
| 2 | 5.25 | 16.8390 | 33.11 |
| 3 | 6.07 | 14.5727 | 79.46 |
| 4 | 6.41 | 13.7958 | 295.89 |
| 5 | 6.77 | 13.0659 | 75.28 |
| 6 | 7.50 | 11.7852 | 28.93 |
| 7 | 9.06 | 9.7607 | 15.21 |
| 8 | 9.62 | 9.1922 | 62.16 |
| 9 | 11.45 | 7.7266 | 119.85 |
| 10 | 12.32 | 7.1860 | 22.14 |
| 11 | 12.89 | 6.8670 | 12.45 |
| 12 | 13.53 | 6.5427 | 661.51 |
| 13 | 15.38 | 5.7607 | 9.19 |
| 14 | 16.27 | 5.4489 | 384.38 |
| 15 | 18.20 | 4.8740 | 116.72 |
| 16 | 19.31 | 4.5966 | 302.81 |
| 17 | 20.36 | 4.3613 | 1000.00 |
| 18 | 21.49 | 4.1346 | 62.49 |
| 19 | 22.75 | 3.9083 | 223.09 |
| 20 | 23.52 | 3.7824 | 240.77 |
| 21 | 24.33 | 3.6580 | 104.39 |
| 22 | 24.78 | 3.5936 | 20.12 |
| 23 | 26.88 | 3.3173 | 117.24 |
| 24 | 27.47 | 3.2472 | 728.94 |
| 25 | 28.92 | 3.0875 | 11.18 |
| 26 | 30.68 | 2.9146 | 72.66 |
| 27 | 31.70 | 2.8227 | 15.96 |
| 28 | 32.21 | 2.7795 | 13.99 |
| 29 | 34.27 | 2.6169 | 17.89 |
| 30 | 34.99 | 2.5647 | 29.78 |
| 31 | 35.53 | 2.5266 | 21.55 |
| 32 | 36.80 | 2.4426 | 13.14 |
| 33 | 37.37 | 2.4063 | 15.25 |
| 34 | 39.13 | 2.3022 | 8.44 |

Figure 3:
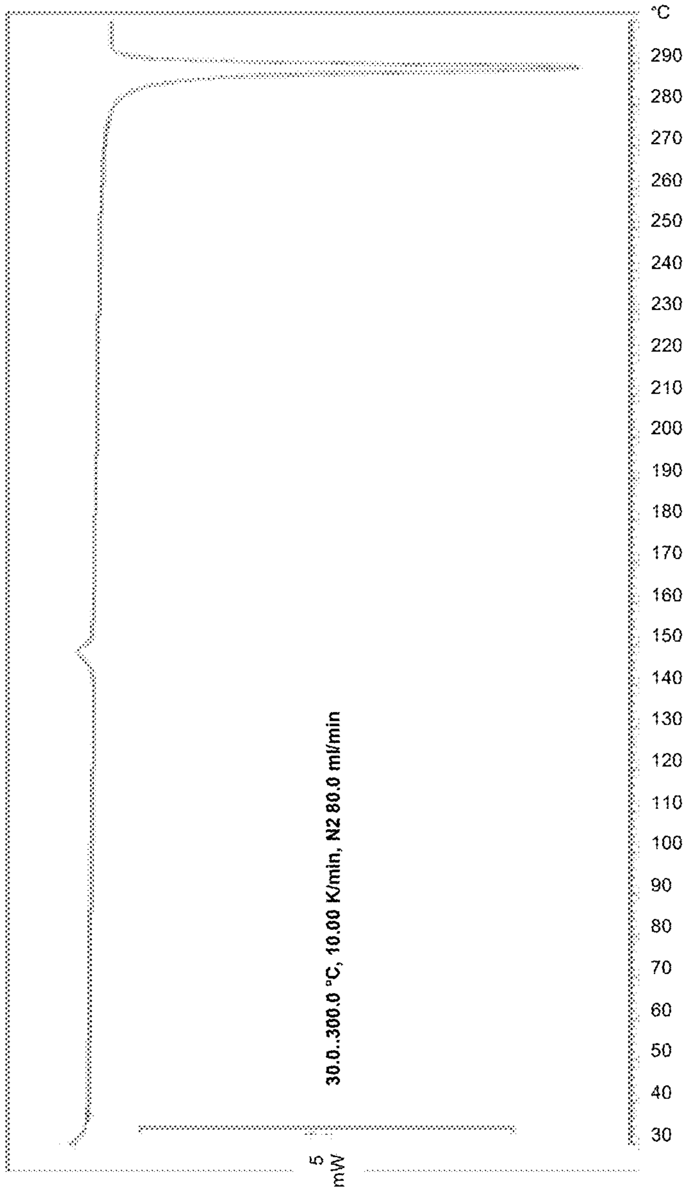
FIG. 3 shows the differential scan calorimetry (DSC) curve of the solid form alpha of 2-(3,5-dichlorophenyl)-1,3-benzoxazole-6-carboxylic acid (11 mg; 30-300° C.; 10° C./min).
Figure 4:
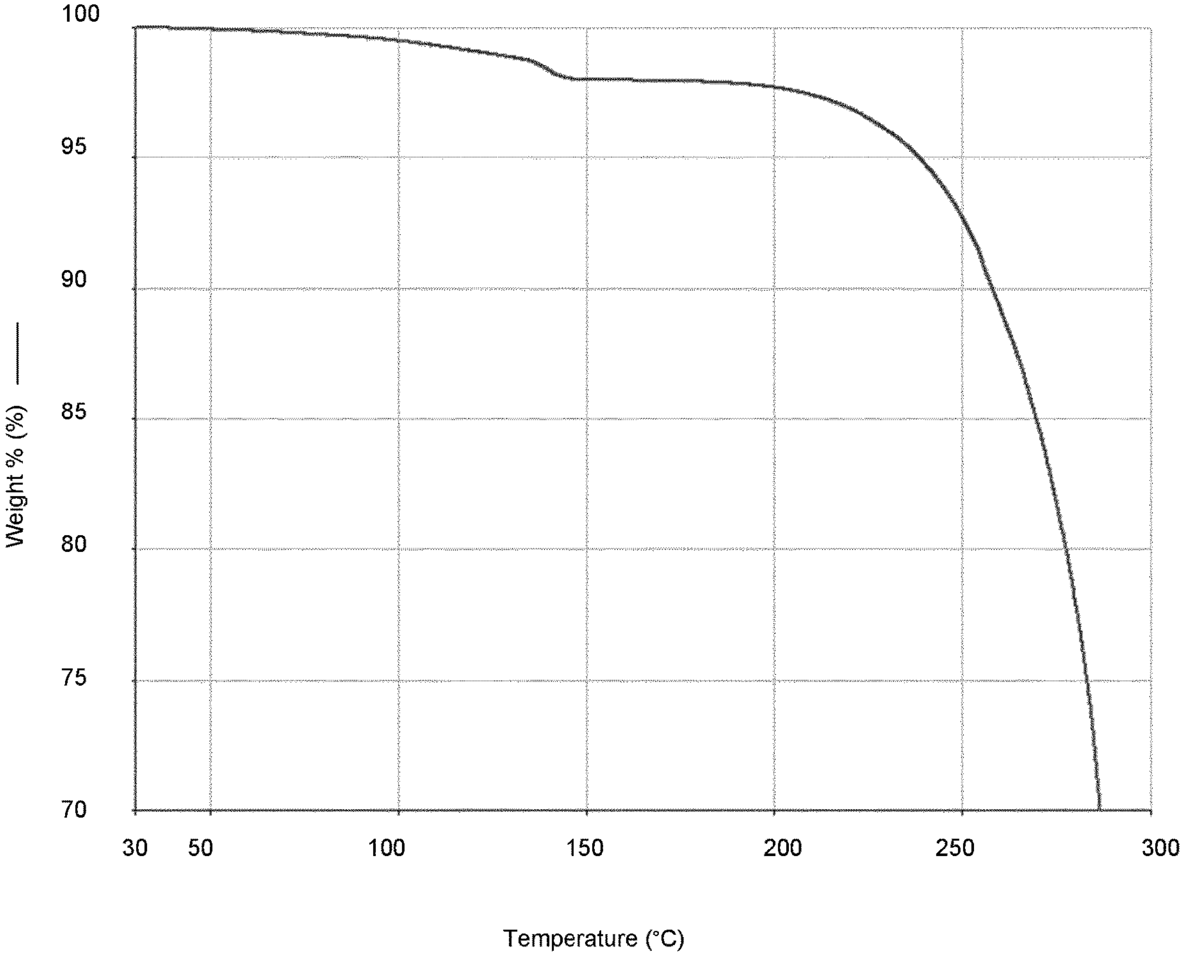
FIG. 4 shows the thermogravimetric analysis (TGA) curve of the solid form alpha of 2-(3,5-dichlorophenyl)-1,3-benzoxazole-6-carboxylic acid (5° C./min, 30-300° C.).
Figure 5:
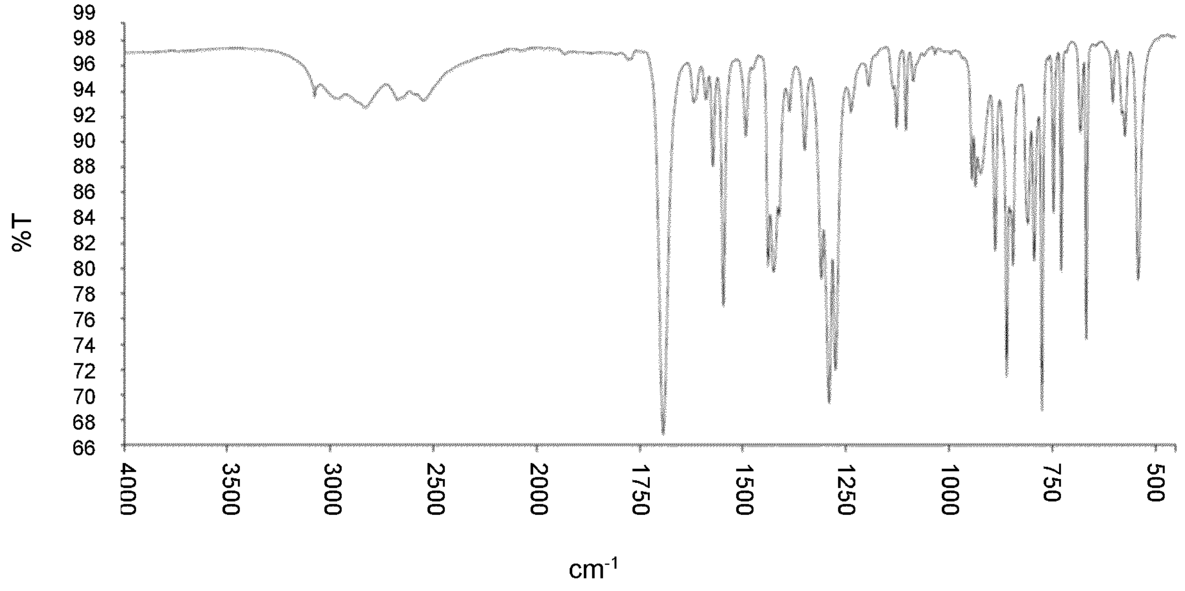
FIG. 5 shows the infrared (IR) spectrum of the solid form alpha of 2-(3,5-dichlorophenyl)-1,3-benzoxazole-6-carboxylic acid.

In a preferred embodiment, the present invention relates to the crystalline form alpha as described above, further characterized by a DSC profile similar to that shown in FIG. 3, i.e. having an exothermic transition in the range from about 135 to about 165° C. and an endothermic one with a peak at 287±2° C., and/or by a TGA profile representing a thermal behavior as shown in FIG. 4 and/or an IR spectrum having at least one of 1695, 1573, 1547, 1437, 1420, 1298, 1276, 882, 862, 772, 745, 725, 678, 665, 534 $cm^{-1}$.

Figure 7:
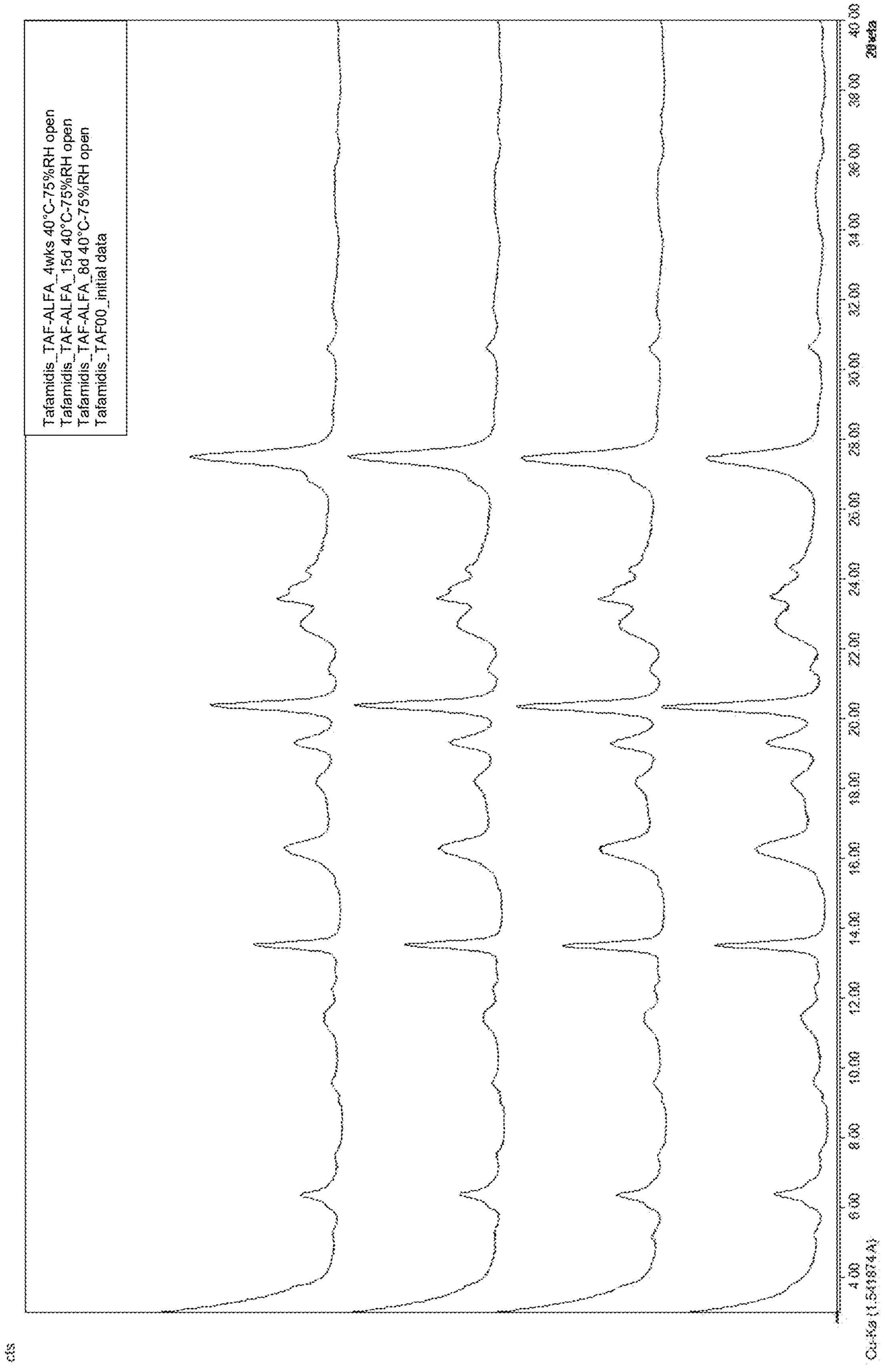
FIG. 7 shows a comparison of the XRPD patterns referred to form alpha of 2-(3,5-dichlorophenyl)-1,3-benzoxazole-6-carboxylic acid during the stability studies, acquired at time zero, 8 days, 15 days and 4 weeks at 40° C. and at 75% of relative humidity (RH) in an open vial.
Figure 8:
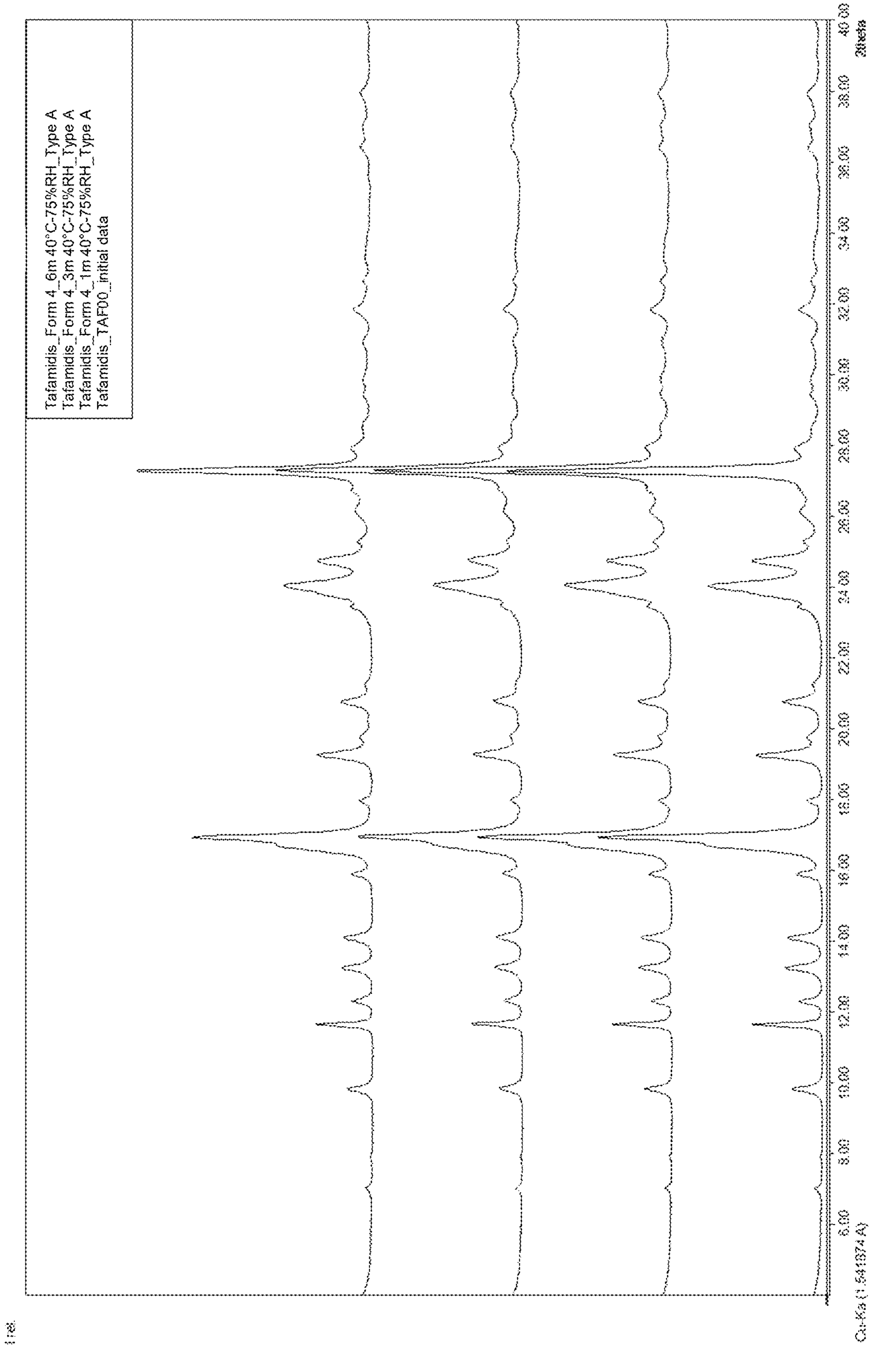
FIG. 8 shows a comparison of the XRPD patterns referred to form 4 of 2-(3,5-dichlorophenyl)-1,3-benzoxazole-6-carboxylic acid during the stability studies, acquired at time zero, 1, 3, 6 months at 40° C. and at 75% of relative humidity (RH).

It was found that form alpha according to the present invention is chemically and physically stable, in that it does not change its polymorphic form and its chemical purity does not decrease over storage between 15 to 60° C. for several weeks at different degree of humidity as reported in FIGS. 7 and 8. This feature permit that form alpha of tafamidis, according to the present invention, can be used as intermediate to produce other crystalline forms of tafamidis (e.g. form 1 or form 4 as described in WO 2016/38500) or salts, such as the meglumine salt, in a substantially pure crystalline form via methods suitable for large-scale production.

In another embodiment, the present invention relates to a process for the preparation of the crystalline form alpha of 2-(3,5-dichlorophenyl)-1,3-benzoxazole-6-carboxylic acid as described above, comprising the steps of:

i. dissolving 2-(3,5-dichlorophenyl)-1,3-benzoxazole-6-carboxylic acid in a solvent selected from the group consisting of tetrahydrofuran, 2-methyltetrahydrofuran and mixtures thereof;
ii. adding the solution obtained in step i. to an anti-solvent selected from the group consisting of hexane, heptane and mixture thereof;
iii. isolating the obtained solid.

Preferably, in said process for the preparation of form alpha, the solvent used for dissolving 2-(3,5-dichlorophenyl)-1,3-benzoxazole-6-carboxylic acid in step i. is tetrahydrofuran.

Preferably, in said process for the preparation of form alpha, the anti-solvent used in step ii. is heptane.

In a preferred embodiment, in the process according to the present invention the weight/volume ratio of tafamidis/solvent is from 1:5 to 1:30, more preferably from 1:18 to 1:28.

In a preferred embodiment, in the process according to the present invention the volume/volume ratio of solvent/anti-solvent is from 1:1 to 1:5, preferably from 1:1.5 to 1:3.5.

In a preferred embodiment, step i. in the process according to the present invention is carried out in the range from 30 to 80° C., more preferably from 40 to 70° C. or from 55 to 65° C.

In a preferred embodiment, step ii. in the process according to the present invention is carried out at from −30 to 25° C., more preferably from −20 to 20° C. or from −15 to 10° C.

In an embodiment, the present invention relates to the use of the crystalline form alpha of 2-(3,5-dichlorophenyl)-1,3-benzoxazole-6-carboxylic acid as defined above for the preparation of a solid form of 2-(3,5-dichlorophenyl)-1,3-benzoxazole-6-carboxylic acid other than form alpha, or of a salt or adduct thereof.

Preferably, the present invention relates to the preparation of form 1 or 4 of 2-(3,5-dichlorophenyl)-1,3-benzoxazole-6-carboxylic acid from solid form alpha.

More preferably the present invention relates to the preparation of form 1 of 2-(3,5-dichlorophenyl)-1,3-benzoxazole-6-carboxylic acid using solid form alpha as an intermediate, wherein said form alpha is suspended in high boiling solvent, e.g. 1,3,5-trimethylbenzene, xylene, chlorobenzene, at a temperature between 100° ° C. and 140° ° C. for 1 to 24 hours, more preferably between 125° C. and 135° C. for 15 to 20 hours. The resulting suspension is maintained under stirring at the same range of temperature for about 24 hours, preferably for about 17 hours, then it is cooled to 20-25° C. and filtered with conventional techniques. The filtered solid is washed with the same solvent used in the reaction and dried under vacuum at 45-50° C. for about 1 to about 24 hours, preferably for about 10 to about 18 hours.

Advantageously, the present invention relates to the preparation of form 4 of 2-(3,5-dichlorophenyl)-1,3-benzoxazole-6-carboxylic acid using solid form alpha as an intermediate, wherein the drying of said form alpha is carried out under vacuum at a temperature between 100° C. and 150° C. for about 1 to about 24 hours, more preferably between 125° C. and 135° C. for about 1 to about 20 hours, preferably for about 10 to about 16 hours.

It was found that crystalline form 1 and crystalline form 4 of tafamidis obtained according to the present invention, are obtained in a substantially pure crystalline form using suitable and scalable processes. Said forms are chemically and physically stable, especially they do not change their XPRD pattern and shows no degradation, if kept at storage condition. Furthermore, analysing the first set of stability data, it is possible to demonstrate that form 4 is chemically and physically stable if stored for several months at 40° C. and 75% of relative humidity (RH).

Figure 12:
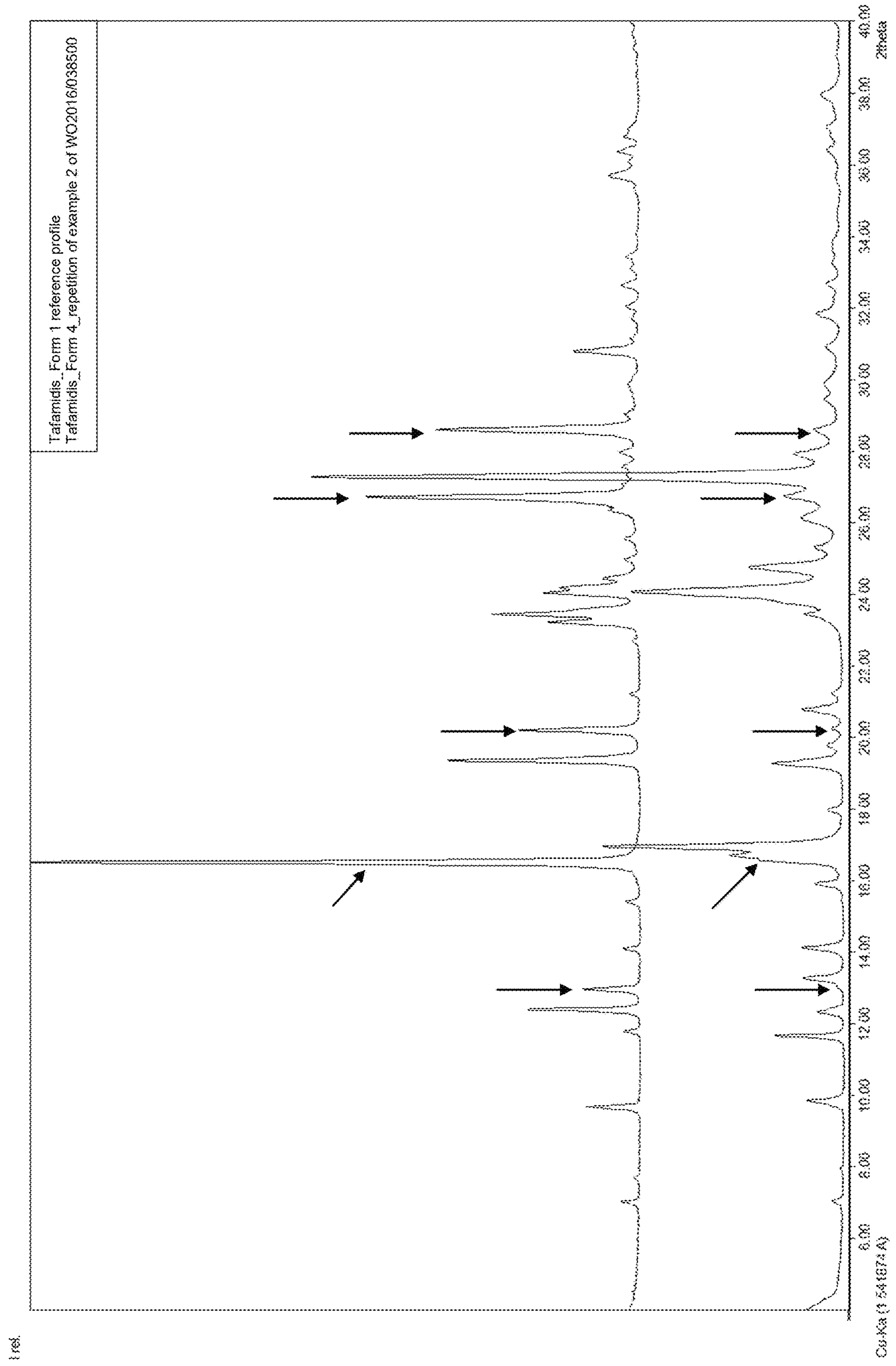
FIG. 12 shows a comparison of the XRPD patterns referred to form 1 of 2-(3,5-dichlorophenyl)-1,3-benzoxazole-6-carboxylic acid and form 4 obtained from the repetition of example 2 of WO2016/038500.

By contrast, it was found that solid tafamidis, obtained by reproducing on multigram scale the methods of the prior art, e.g. example 2 of WO2016/038500 as reported as not limiting example in the experimental part, contained detectable amounts of crystalline forms other than form 4 as shown in FIG. 12.

In a preferred embodiment, the present invention relates to the preparation of a salt of tafamidis, preferably the meglumine salt of tafamidis, starting from solid form alpha of tafamidis.

Preferably tafamidis meglumine salt is obtained by suspending form alpha in a mixture of solvents selected from the group consisting of methyl, ethyl, propyl and isopropyl alcohol and water at 20-25° C. More preferably, form alpha is suspended in a mixture consisting of isopropyl alcohol and water respectively in the volume ratio ranging from about 3:1 to about 6:1, preferably 5:1. Then meglumine is added and the resulting suspension is heated until complete dissolution. After cooling the obtained solution to 10-15° C. for about 1 to about 5 hours, preferably for about 1-2 hours, tafamidis meglumine salt is recovered by conventional filtration techniques, washed with the same solvent mixture, used during the reaction and dried under vacuum at about 45-50° C. for about 1 to about 20 hours, preferably for about 10 to about 16 hours. The first set of stability data shows that tafamidis meglumine salt, is obtained following the present invention in a substantially pure and stable polymorphic form M.

In an embodiment, the present invention provides a pharmaceutical formulation comprising the crystalline form alpha of 2-(3,5-dichlorophenyl)-1,3-benzoxazole-6-carboxylic acid and, optionally, at least one excipient.

The following examples are provided to illustrate specific embodiments of the present invention, without intention to limit its scope.

The instruments and methods used to characterize the crystals obtained in the examples are as follows:

X-ray powder diffraction analyses (XRPD) were performed on a Bruker D8 Advance X-ray powder diffractometer at about 25° C. and ambient humidity (e.g. 25-35%), using a Cu Kα tube (40 kV, 40 mA, λ=1.5418 Å) as the X-ray source, equipped with a linear Lynxeye XE-T position sensitive detector set at 250 mm from the sample. A Nickel filter (0.0125 mm thickness) was mounted on the primary beam. Data collection was made in coupled mode, theta-theta configuration over an angular range between at least 3° 2 theta and 40° 2theta and a scan step of 0.02°. Fine powder samples were placed in a flat, thin layer in the 12 mm×0.2 mm cavity of a silicon low background plate fixed on a sample holder fitting an autosampler position. The instrument was previously calibrated by means of NIST SRM 1976b. Data acquisition was performed by means of Bruker Diffraction Measurement Center software; data elaboration was performed by means of Crystal Impact Match! or Bruker Diffrac. EVA software.

Differential scan calorimetry (DSC): DSC tests were conducted by use of a Mettler-Toledo DSC1 Stare System. Indium was used for calibration. Accurately weighed samples (3-5 mg) were placed in open aluminum vented pans and heated at a rate of 10° C./min under 80 mL/min nitrogen purge. Range from 30° C. up to 300° C. was investigated.

TGA analysis was carried out by means of a Perkin-Elmer Pyris 1 TGA at the scan rate of 5° C./min in the thermal range of 30-300° C. and under nitrogen flow.

About 5 mg of powder were loaded in the platinum crucible of the thermobalance.

Fourier transform Infrared analysis (FT-IR): FT-IR analyses were performed with a Spectrum Two FTIR Spectrophotometer equipped with a universal Attenuated Total Reflectance (ATR) and a Spectrum 10™ Software. Measurements were performed by carrying out 16 scans with a resolution of 4.0 $cm^{-1}$ in a range between 4000 and 450 $cm^{-1}$.

Tafamidis used in the experiment is prepared according to the procedures described in prior art, e.g. to that reported in Proc. Natl. Acad. Sci USA, Tafamidis, a potent and selective transthyretin kinetic stabilizer that inhibits the amyloid cascade, 2012 June, 109(24), 9629-34.

Example 1

Preparation of Tafamidis Form Alpha.

Tafamidis (10 g) was dissolved in tetrahydrofuran (220 mL) at 60-65° C. The resulting solution was filtered through a diatomaceous earth (Hyflo®) bed. Filtrate was heated to 60-65° C. and the obtained clear solution was added dropwise to heptane (730 mL) cooled to −15/−10° ° C. The resulting suspension was maintained under stirring at the same temperature for 1-2 hours and then filtered. Solid was dried under vacuum at 45-50° C. for 16 hours and analyzed by XRPD.

Tafamidis form alpha was obtained.

Yield: 8.5 g

Example 2

Preparation of Tafamidis Form 4

Tafamidis form alpha (8.5 g) obtained according to the procedure in example 1 was dried under vacuum at 130° C. for 2 hours. The obtained solid was analyzed by XRPD.

Figure 10:
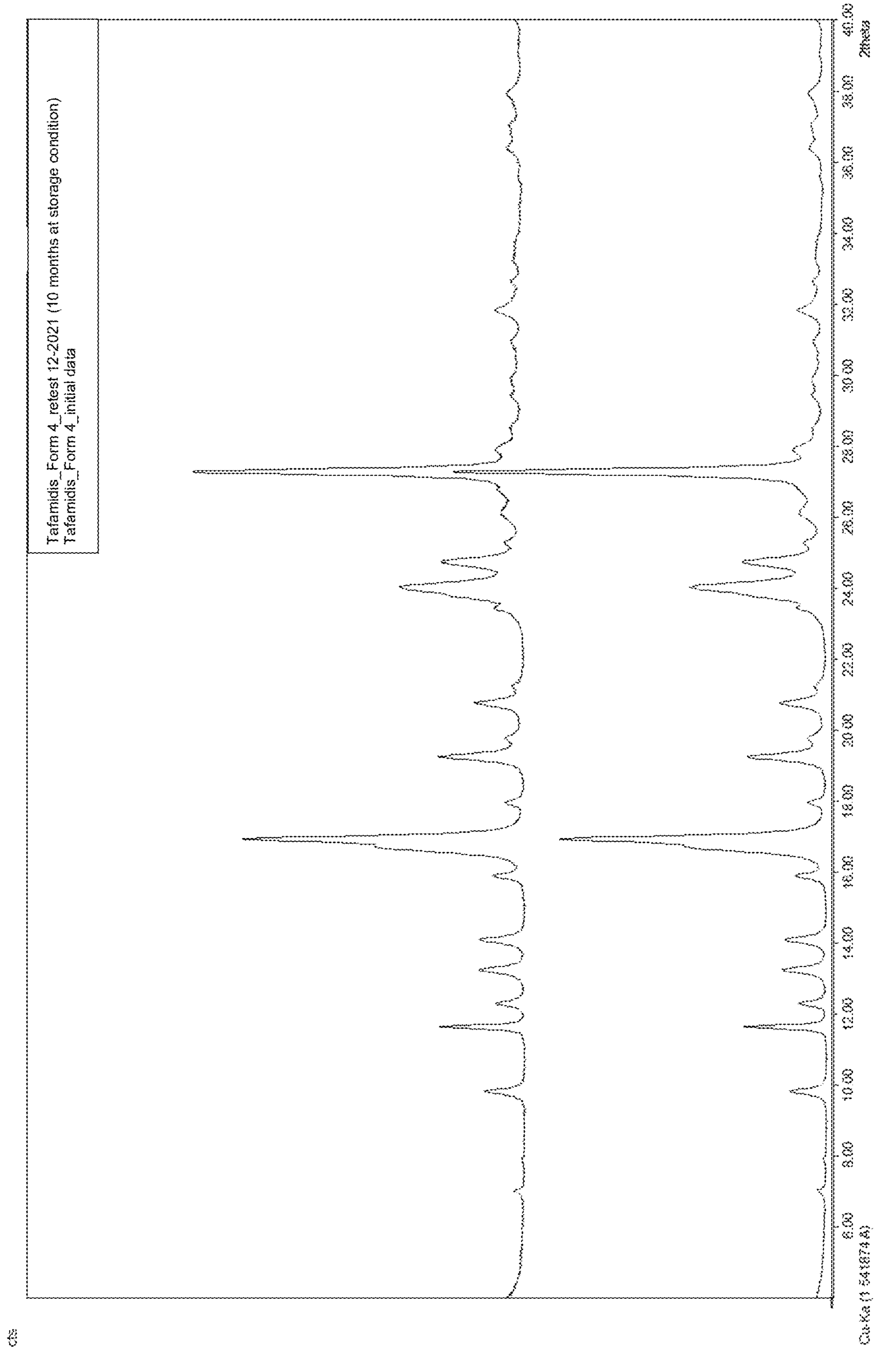
FIG. 10 shows a comparison of the XRPD patterns referred to form 4 of 2-(3,5-dichlorophenyl)-1,3-benzoxazole-6-carboxylic acid kept at storage condition acquired at time zero and 10 months in a close vial.

Tafamidis was obtained in a substantially pure crystalline form 4, as shown in FIG. 10 (initial data).

The obtained tafamidis form 4 does not change its XRPD pattern if kept in a close vial at storage condition for 10 months as shown in FIG. 10.

Yield: 8.5 g

Example 3

Preparation of Tafamidis Form 1

Tafamidis form alpha (3 g) was suspended in 1,3,5-trimethylbenzene (mesitylene) (30 mL) and heated to 130-135° C. Resulting suspension was maintained under stirring at the same temperature for 17 hours, then cooled to 20-25° C. and filtered. Solid was washed with mesitylene (5 mL), dried under vacuum at 45-50° C. for 16 hours and analysed by XRPD. Tafamidis was obtained in substantially pure crystalline form 1, as shown in FIG. 9 (initial data).

Figure 9:
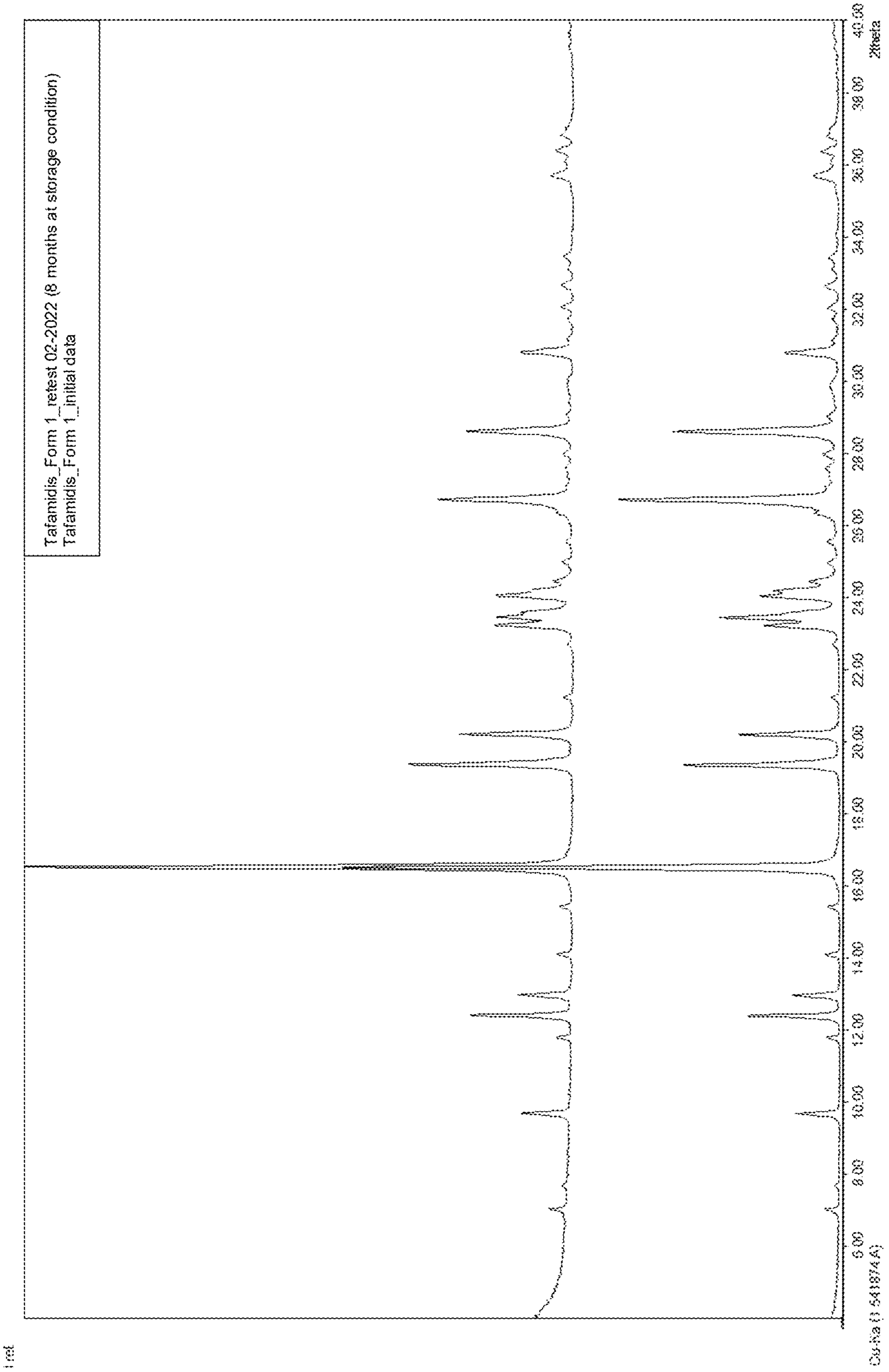
FIG. 9 shows a comparison of the XRPD patterns referred to form 1 of 2-(3,5-dichlorophenyl)-1,3-benzoxazole-6-carboxylic acid kept at storage condition acquired at time zero and 8 months in a close vial.

The obtained tafamidis form 1 does not change its XRPD pattern if kept in a close vial at storage condition for 8 months as shown in FIG. 9. Yield: 3 g

Example 4

Preparation of Tafamidis Meglumine (Form M)

Tafamidis form alpha (10 g) was suspended in a mixture of solvents isopropyl alcohol/water 5:1 (300 mL) at 20-25° C. Meglumine (6.8 g, 1.07 eq.) was added and resulting suspension was dissolved at 80° C. Obtained solution was slowly cooled to 10-15° C. Resulting suspension was maintained under stirring at the same temperature for 1-2 hours and then filtered. Solid was washed with the same mixture of solvents (15 mL), dried under vacuum at 45-50° C. for 16 hours and analysed by XRPD.

Figure 11:
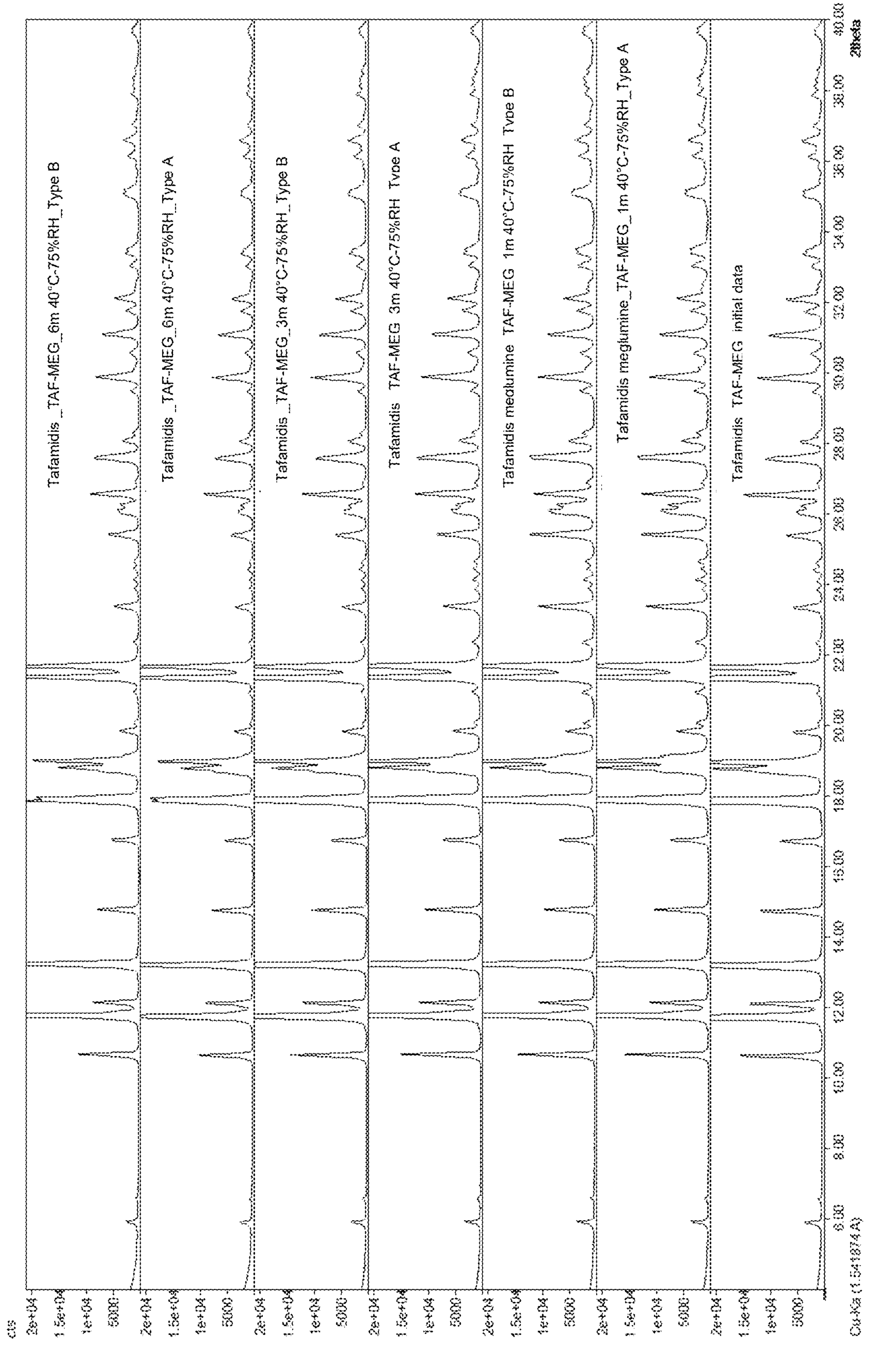
FIG. 11 shows a comparison of the XRPD patterns referred to 2-(3,5-dichlorophenyl)-1,3-benzoxazole-6-carboxylic meglumine salt during the stability studies, acquired at time zero, 1, 3, 6 months at 40° C. and at 75% of relative humidity (RH).

Tafamidis meglumine was obtained in substantially pure crystalline form M, as shown in FIG. 11 (initial data)

Yield: 14.9 g

Example 5

Preparation of Tafamidis Form 4 from Wet Form Alpha

Tafamidis (15 Kg) was dissolved in tetrahydrofuran (375 L) at 55-60° C. The resulting solution was filtered through a diatomaceous earth (Hyflo®) bed. Filtrate was heated to 55-60° C. and the obtained clear solution was added dropwise to heptane (750 L) cooled to −15/−10° C. The resulting suspension was maintained under stirring at the same temperature for 1-2 hours and then filtered. Solid was dried under vacuum at 120-125° C. for several hours, until the completed conversion to form 4 was achieved.

Yield: 14.2 kg

Example 6 (Comparative): Preparation of Tafamidis Form 4

(Repetition of Example 2 of WO2016/038500 on Multigram Scale)

Tafamidis form 1 (5 g) was suspended in tetrahydrofuran (200 mL) and the mixture was heated at 75° C.

The hot solution was filtered on a pre-warmed 0.2 μηi nylon filter into a vessel, cooled with an ice/water bath, containing toluene (670 mL)

The obtained solution was stored overnight in a refrigerator (−10/−15° C.).

The obtained solid was filtered and dried under vacuum.

The solid analysed by XRPD, FIG. 12, shows that using this experimental procedure on multigram scale Tafamidis in its polymorphic form 4 contaminated with polymorphic form 1 was obtained.

Yield: 2 g

Example 7: Stability Studies 7 a. Form Alpha

Vials containing 100 mg each of alpha form of present invention are stored at the following conditions, wherein RH is referred to relative humidity:

room Temperature (RT) and 80% RH, open vial

40° C. and 75% RH, open vial

The sample were analysed before the storage (initial data), 8 days, 15 days and 4 weeks using X-ray powder diffractogram (XRPD) to evaluate any change in crystalline form and using HPLC to measure the chemical purity.

Figure 6:
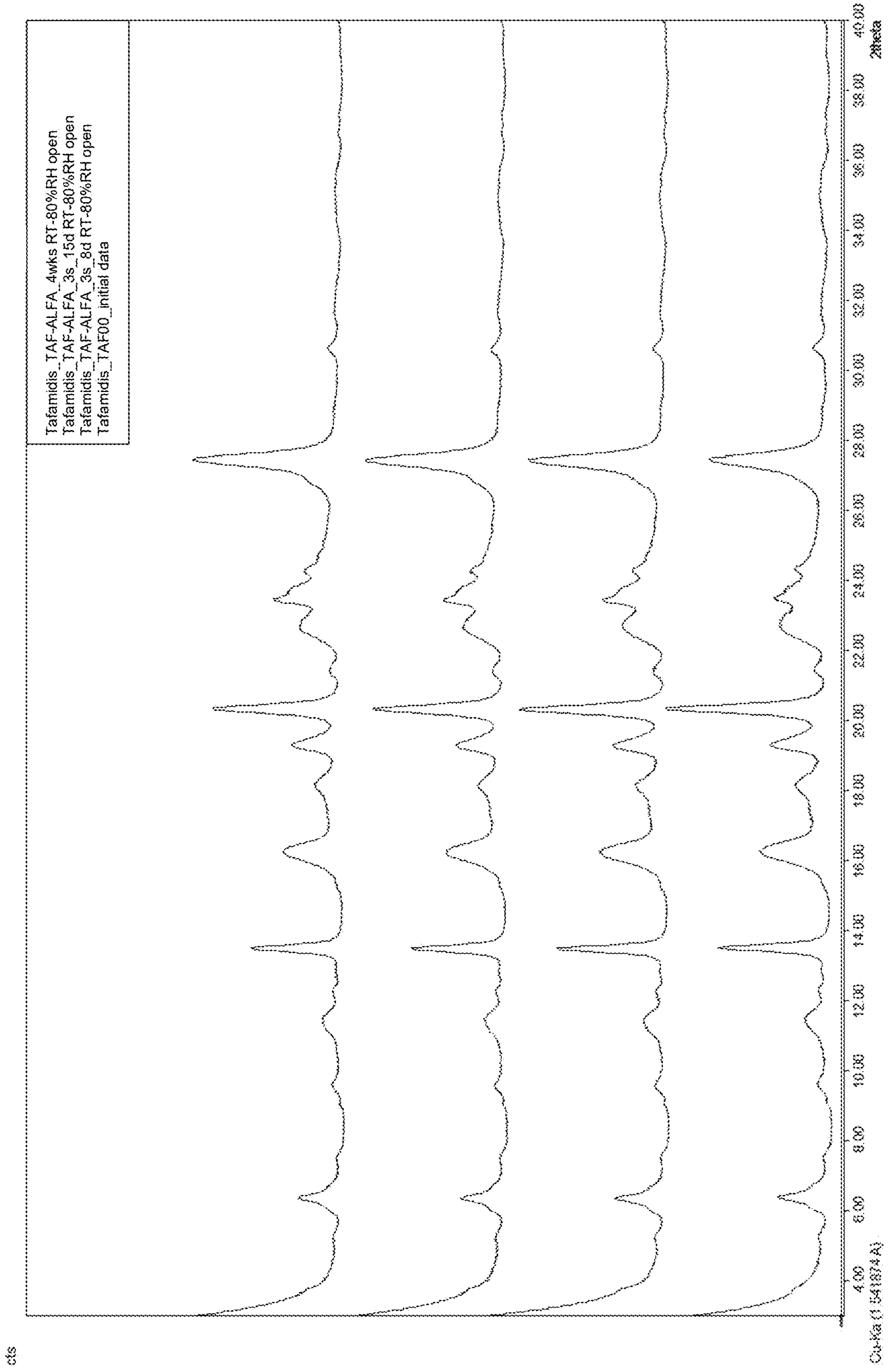
FIG. 6 shows a comparison of the XRPD patterns referred to form alpha of 2-(3,5-dichlorophenyl)-1,3-benzoxazole-6-carboxylic acid during the stability studies, acquired at time zero, 8 days, 15 days and 4 weeks at room temperature and at 80% of relative humidity (RH) in an open vial.

The X-ray powder diffractograms (XRPD) recorded after 4 weeks show no signs of transformation of alpha form into a different crystalline form as reported in FIGS. 6 and 7.

The HPLC analysis show that alpha form of the present invention does not present a significant worsening of the purity, in terms of formation of new impurities and increase of the content of those already present profile with respect to the initial acquired profile.

7 b. Form 4 Obtained from Form Alpha 700 mg of tafamidis form 4 of obtained according to present invention are stored at the following conditions, wherein RH is referred to relative humidity:

40° C. and 75% RH, type A container.

The samples were analysed before the storage (initial data), after 1 month, 3 months, 6 months using X-ray powder diffractogram (XRPD) to evaluate any change in crystalline form and using HPLC to measure the chemical purity.

The X-ray powder diffractogram (XRPD) recorded after 6 months shows no signs of transformation into a different crystalline form as reported in FIG. 8.

The HPLC analysis show that alpha form of the present invention does not present a significant worsening of the purity, in terms of formation of new impurities and increase of the content of those already present profile with respect to the initial acquired profile.

The invention claimed is:

1. A crystalline form of 2-(3,5-dichlorophenyl)-1,3-benzoxazole-6-carboxylic acid, characterized by an XRPD profile comprising the peaks at 6.4, 9.6, 13.5, 16.3, 18.2, 20.4 and 27.5 degrees 2θ, when collected with the Kα radiation of copper (λ=1.5418 Å).

2. The crystalline form of 2-(3,5-dichlorophenyl)-1,3-benzoxazole-6-carboxylic acid according to claim 1, characterized by an XRPD profile additionally comprising at least one of the peaks at 5.3, 12.3, 19.3, 22.8 and 23.5 degrees 2θ.

3. The crystalline form of 2-(3,5-dichlorophenyl)-1,3-benzoxazole-6-carboxylic acid according to claim 1, being characterized by a DSC profile having an exothermic transition in the range from 135 to 165° C. and an endothermic transition with a peak at 287±2° C.

4. The crystalline form of 2-(3,5-dichlorophenyl)-1,3-benzoxazole-6-carboxylic acid according to claim 2, being characterized by a DSC profile having an exothermic transition in the range from 135 to 165° C. and an endothermic transition with a peak at 287±2° C.

5. The crystalline form of 2-(3,5-dichlorophenyl)-1,3-benzoxazole-6-carboxylic acid according to claim 1, being characterized by a TGA profile having a thermal behavior as shown in FIG. 4.

6. The crystalline form of 2-(3,5-dichlorophenyl)-1,3-benzoxazole-6-carboxylic acid according to claim 2, being characterized by a TGA profile having a thermal behavior as shown in FIG. 4.

7. The crystalline form of 2-(3,5-dichlorophenyl)-1,3-benzoxazole-6-carboxylic acid according to claim 3, being characterized by a TGA profile having a thermal behavior as shown in FIG. 4.

8. The crystalline form of 2-(3,5-dichlorophenyl)-1,3-benzoxazole-6-carboxylic acid according to claim 4, being characterized by a TGA profile having a thermal behavior as shown in FIG. 4.

9. A process for the preparation of the crystalline form of 2-(3,5-dichlorophenyl)-1,3-benzoxazole-6-carboxylic acid according to claim 1, comprising the steps of:

i. dissolving 2-(3,5-dichlorophenyl)-1,3-benzoxazole-6-carboxylic acid in a solvent selected from the group consisting of tetrahydrofuran, 2-methyltetrahydrofuran or mixture thereof ii. adding the solution obtained in step i. to an anti-solvent selected from the group consisting of hexane, heptane or mixture thereof;

iii. isolating the obtained solid.

10. The process according to claim 9, wherein the solvent used for dissolving 2-(3,5-dichlorophenyl)-1,3-benzoxazole-6-carboxylic acid in step i. is tetrahydrofuran.

11. The process according to claim 9, wherein the anti-solvent used in step ii. is heptane.

12. A process for preparing form 1 of 2-(3,5-dichlorophenyl)-1,3-benzoxazole-6-carboxylic acid, wherein solid form alpha of 2-(3,5-dichlorophenyl)-1,3-benzoxazole-6-carboxylic acid as defined in claim 1 is suspended in a high-boiling solvent at a temperature between 100° C. and 140° C. for 1 to 24 hours, followed by cooling the suspension to 20-25° C., and filtering of the cooled suspension.

13. The process according to claim 12, wherein the filtered solid is washed with the high-boiling solvent and dried under vacuum at 45-50° C. for about 1 to about 24 hours.

14. A process for preparing form 4 of 2-(3,5-dichlorophenyl)-1,3-benzoxazole-6-carboxylic acid, wherein solid form alpha of 2-(3,5-dichlorophenyl)-1,3-benzoxazole-6-carboxylic acid as defined in claim 1 is dried under vacuum at a temperature between 100° C. and 150° C. for about 1 to about 24 hours.

* * * * *